United States Patent [19]

Heartness

[11] Patent Number: 4,583,949

[45] Date of Patent: Apr. 22, 1986

[54] PARTIAL VACUUM STABILIZER FOR DENTAL PROSTHESIS

[76] Inventor: Olaf A. Heartness, 2493 New York Ave., Melville, N.Y. 11747

[21] Appl. No.: 619,046

[22] Filed: Jun. 11, 1984

[51] Int. Cl.[4] .............................................. A61C 13/24
[52] U.S. Cl. ................................................... 433/185
[58] Field of Search ...................... 433/185, 188, 184

[56] References Cited

U.S. PATENT DOCUMENTS

| | | | |
|---|---|---|---|
| 1,354,938 | 10/1920 | Angel | 433/188 |
| 1,714,185 | 5/1929 | Morgan | 433/188 |
| 2,029,945 | 2/1936 | Rubinstein | 433/185 |
| 2,085,268 | 6/1937 | Nouel | 433/185 |
| 2,897,594 | 8/1959 | Kopec et al. | 433/185 |
| 3,644,997 | 2/1972 | Fernandez | 433/184 |
| 3,722,096 | 3/1973 | Kopfer et al. | 433/184 |
| 4,204,322 | 5/1980 | Johnson et al. | 433/185 |

FOREIGN PATENT DOCUMENTS

| | | | |
|---|---|---|---|
| 481606 | 12/1916 | France | 433/185 |
| 358543 | 1/1962 | Switzerland | 433/184 |

Primary Examiner—John J. Wilson
Attorney, Agent, or Firm—John Cyril Malloy

[57] ABSTRACT

A dental prosthesis of the type secured to the alveolar ridge within the mouth of the user through the application of a partial vacuum which serves to stabilize and maintain a dental plate in secure operative position. A full or partial dental plate incorporates false teeth at least some of which have a hollow interior portion in which valve means are mounted in fluid communication with a pressure differential channel itself extending along and being disposed in fluid communication with exposed surface portions of the alveolar ridge. Application of negative pressure to the interior of the mouth serves to direct fluid flow from the differential pressure channel through the valving structure within the hollow interior portion wherein such valving structure prohibits reverse flow therethrough. A partial vacuum is thereby created and maintained between the undersurface of the dental plate, in the area of the differential pressure channel, and the exposed surface of the alveolar ridge.

20 Claims, 30 Drawing Figures

PARTIAL VACUUM STABILIZER FOR DENTAL PROSTHESIS

BACKGROUND OF THE INVENTION

1. Field of the Invention

The present invention is directed towards a dental prosthesis in the form of a full or partial plate specifically structured to create and maintain a partial vacuum of predetermined negative pressure between the undersurface of the dental plate and the exposed surface of the alveolar ridge on which the plate is mounted so as to establish and maintain the occlusive seal between the plate and the ridge and thereby insure proper positioning of the plate within the mouth of the user.

2. Description of the Prior Art

Problems associated with the proper fitting and positioning of dentures in the mouth of denture wearers have long been recognized in the prior art. Difficulties are primarily directed to the maintenance of an occlusive seal between the wearer's gum in the area of the alveolar ridge and the undersurface of the dental prosthesis or dental plate. This is especially true in the use of full dentures or substantially complete set of false teeth. Utilizing numerous prior art techniques of establishing the occlusive seal and the positioning of the dental plates, such seal can readily be broken during eating. This occurs most frequently when the denture wearer bites into a relatively hard object such as an apple wherein the false teeth are gripped by the object being chewed. At times uneven pressure by the jaws applied to the dental plate on one side or at one point causes the plate to tip and thereby break the seal along the gum line between the undersurface of the dental plate and the alveolar ridge. When such happens, the dentures will of course separate from the upper and lower jaw gums resulting in inability to function, discomfort and frequent embarrassment to the dental wearer.

Prior art attempts to overcome such situations and maintain the occlusive seal include the manufacture of the dental plates in an accurate manner to accomplish a close fit. Further, a sealing medium such as a paste or adhesive-like powder is applied to the undersurface or sealing side of the dental plate and the occlusive seal is established therebetween and the exposed surface of the alveolar ridge.

In addition, prior art attempts to mount and maintain denture plates in their proper position include the application of a partial vacuum of established or variable negative pressure between the undersurface of the plate and the exposed surface of the gum or alveolar ridge on which the plates are mounted. United States patents which are directed to structures of the type set forth above include: U.S. Pat. Nos. 1,354,938; 1,714,185; 2,029,945; 2,085,268; 2,897,594; 3,644,997; and 3,722,096. While structures of the type set forth in the above noted United States patents are operable when constructed in the manner set forth therein, frequently devices of this type are less than efficient or are overly complicated which detracts both in their manufacture and utilization.

Accordingly, there is a need in the dental prosthesis art for a design and structure capable of insuring the maintenance of the desired occlusive seal between a denture plate and the gum portion on which it is mounted. Such structure should be capable of easy insertion and removal and should be effective to maintain the desired occlusive seal during eating or other normal bodily functions.

SUMMARY OF THE INVENTION

The present invention is directed towards dental prosthesis incorporating stabilizing structure so as to maintain proper position of dentures within the mouth of the wearer through the establishment and maintenance of a partial vacuum between the undersurface of the full or partial dental plate and the exposed surface of the alveolar ridge on which the plate is mounted. Further, the structure incorporated in the present invention is such as to establish a required partial vacuum of predetermined negative pressure in a simple and efficient manner. The required negative pressure is established by utilizing the tongue and throat muscles in a manner which is similar to the action taken when one drinks a liquid through a straw. More specifically, the tongue and throat muscles are retracted to create a volume of air having less pressure than atmospheric pressure, thereby creating a negative pressure within the mouth. Such negative pressure creates fluid flow, due to the structural components of the present invention, from a differential pressure channel formed in the undersurface of the portion of the dental plate mounted on and conforming to the exposed surface of the alveolar ridge on which the plate is positioned. The fluid flow passes from the aforementioned channel to the exterior of the dental plate thereby creating a partial vacuum of predetermined negative pressure between the undersurface of the plate and the exposed surface of the alveolar ridge. Such partial vacuum is maintained due to proper valving structure located along the path of fluid flow within hollow interior portions of false teeth secured to the exposed surface of the dental plate.

More specifically, the present invention comprises a dental plate, which may be either a full set of dentures or a partial set of dentures, wherein the plate includes an undersurface portion. This undersurface portion has a substantially concave groove-like configuration which is precisely fitted to the alveolar ridge on which it is intended to be mounted. The accuracy of such fit insures a proper sealed engagement between the exposed surface of the gums on which the plate rests and the undersurface of the plate itself. An elongated channel is integrally formed in the undersurface of the plate substantially along the entire length of the undersurface which engages the alveolar ridge.

This differential pressure channel is disposed in direct fluid communication with a hollow interior portion of false teeth mounted on the exposed surface of the dental plate. This hollow interior portion is defined by a first and a second chamber respectively defined by outer casing means which are duplicated to represent individual false teeth. Direct communication is established through proper apertures or passages between the differential pressure chamber and the first of the two chambers. The second of the two chambers is disposed in direct fluid commnication with surrounding atmosphere on the exterior of the hollow interior portion of the false teeth on the inside of the mouth.

Valve means is mounted within the hollow interior portion and is specifically structured to establish and regulate fluid flow between the differential pressure chamber and atmosphere or the exterior of the hollow interior portion. Such valve means includes a first one-way flow valve mounted primarily in the second chamber but including a conduit means which establishes fluid communication between the first chamber and the second chamber. An aperture or like passage is formed within the second false tooth which defines the outer casing of the second chamber such that the second chamber communicates directly with the surrounding atmosphere on the outside of the false teeth. As set forth above, fluid communication is established between the first and second chambers by virtue of the structure and position of the one-way flow valve. A fluid communication is established between the first chamber and the differential pressure channel through the provision of additional passage means. Accordingly, the creation of a vacuum or of a negative pressure within the mouth of the wearer will create fluid flow, due to the established negative pressure, from the differential pressure channel into the first chamber and from the first chamber, through the one-way flow valve into the second chamber. Fluid flow continues to pass from the second chamber out through the aforementioned passage or aperture in the wall of the second false tooth structure from the exterior of the hollow interior portion of the false teeth. This fluid flow is created because of the tendency to equalize pressure within a given space in accordance with Pascal's Law.

The structure and disposition of the one-way flow valve within the second chamber is such as to prohibit fluid flow in the reverse direction once the negative pressure or partial vacuum within the mouth has been eliminated, such as by opening the mouth or the like. Therefore, a partial vacuum of predetermined negative pressure has been established between the undersurface of the dental plate, in the area and along the length of the differential pressure channel, and the exposed surface of the alveolar ridge on which the plate is mounted. The maintenance of this predetermined negative pressure insures the maintenance of the occlusive seal between the plate and gum and thereby assures the wearer that the dental plate will not become inadvertently dislodged or slip during chewing, eating, etc.

The valve means of the present invention further comprises a venting valve located within the first chamber of the first false tooth. Such venting valve comprises a valve seat which includes an aperture formed in an exposed wall of the first tooth which establishes direct fluid communication between the exterior of the hollow interior portion and the first chamber. The venting valve is structured to include a biasing means which normally biases the valve head into closed, sealing engagement with the aperture or valve seat. When in such closed position, the venting valve also prohibits fluid flow from the exterior of the false teeth or hollow interior portion through the first chamber and into the differential pressure channel. However, the valve head of this venting valve is accessible through the aforementioned aperture such that it can be manually displaced out of sealing engagement with the valve seat so as to allow fluid flow. Again in accordance with the principles of Pascal's Law, fluid will flow from the exterior of the hollow interior portion through the first chamber and into the differential pressure channel based on the existence of a negative pressure therein. Once flow is established, the partial vacuum will of course be eliminated and the pressure will be the same along the length of the differential pressure channel and the interior of the mouth. The plate can thereby easily be removed once the partial vacuum has been eliminated.

Within the mouth, the aforementioned alveolar ridge is the bony structure that holds and supports the teeth in each jaw. Also, in a toothless person, the alveolar ridge is that portion of the gum or mouth which is primarily responsible for supporting and holding dentures in position. A fully grown adult will on the average have an alveolar ridge about 4 inches in length and a width averaging approximately $\frac{3}{8}$ of an inch. Therefore, the surface area of the average adult alveolar ridge as dimensioned above is approximately 1.5 square inches. Experimentation indicates that the average person can with small effort create a negative pressure within the mouth of approximately 4 inches Hg. Based on the accepted constant of 14.7 pounds per square inch being the standard pressure at sea level, 4 inches of Hg. converts to 1.96 psi and 2.94 pounds of total force being exerted on the exposed surface (1.5 square inches) of the alveolar ridge once the aforementioned partial vacuum has been established.

However, the above calculations do not take into consideration the sloping sides of the ridge extending from the base thereof to the top or crown portion. In establishing total force exerted on the exposed surface of the ridge by the positioned dental plate, the aforementioned sloping sides would add approximately 0.75 square inch to the surface area on which a force is exerted. Therefore, at 1.96 psi, total force exerted on the exposed surface area of the alveolar ridge would be 4.41 pounds. This means that 4.41 pounds of force would be required to pull or dislodgge the dental plate from the alveolar ridge. In actual application this may perhaps be too much vacuum or negative force applied to the ridge for the comfort of the denture wearer throughout the day. To reduce this force, the denture wearer would merely have to create a smaller initial volume within the mouth, approximately 2 inches Hg.

Conversely, a denture wearer may want to increase the holding power of the denture in certain instances such as when chewing food. He would then induce a higher partial vacuum, perhaps in the range of from 4 to 6 inches Hg. which would give him assurance that his dentures would not fail under any circumstances. Further, due to the provision of the venting valve set forth above, any established force (negative pressure) between the undersurface of the dental plate and the exposed surface of the alveolar ridge could be reduced simply through the manipulation of the valve head by a fingernail or any convenient tool. By depressing the valve head, the partial vacuum and accordingly the pressure exerted on the surface of the alveolar ridge is reduced thereby accomplishing a more comfortable and yet secure fit.

The invention accordingly comprises the features of construction, combination of elements, and arrangements of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
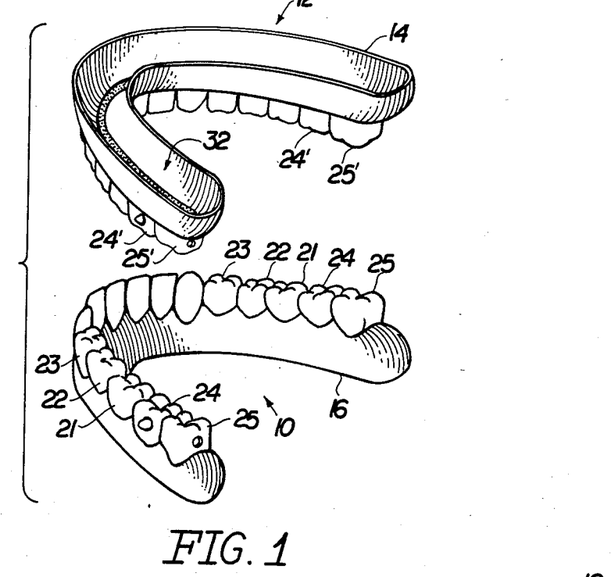
FIG. 1 is an isometric view of both an upper and lower full denture plate incorporating the present invention.

With reference to FIG. 1 the present invention is directed towards a dental prosthesis incorporating the application of a partial pressure to the exposed gum surface of the alveolar ridge in order to maintain lower and upper dental plates 10 and 12 respectively properly positioned within the user's mouth. FIG. 1 relates to the structure of the subject application being incorporated in a full denture plate wherein a full set of false teeth are disclosed. However, it is to be emphasized that the subject invention can be adapted for use in a partial plate or a plate structure incorporating only predetermined ones of false teeth which will be explained in greater detail hereinafter.

Figures 2, 3, 4:
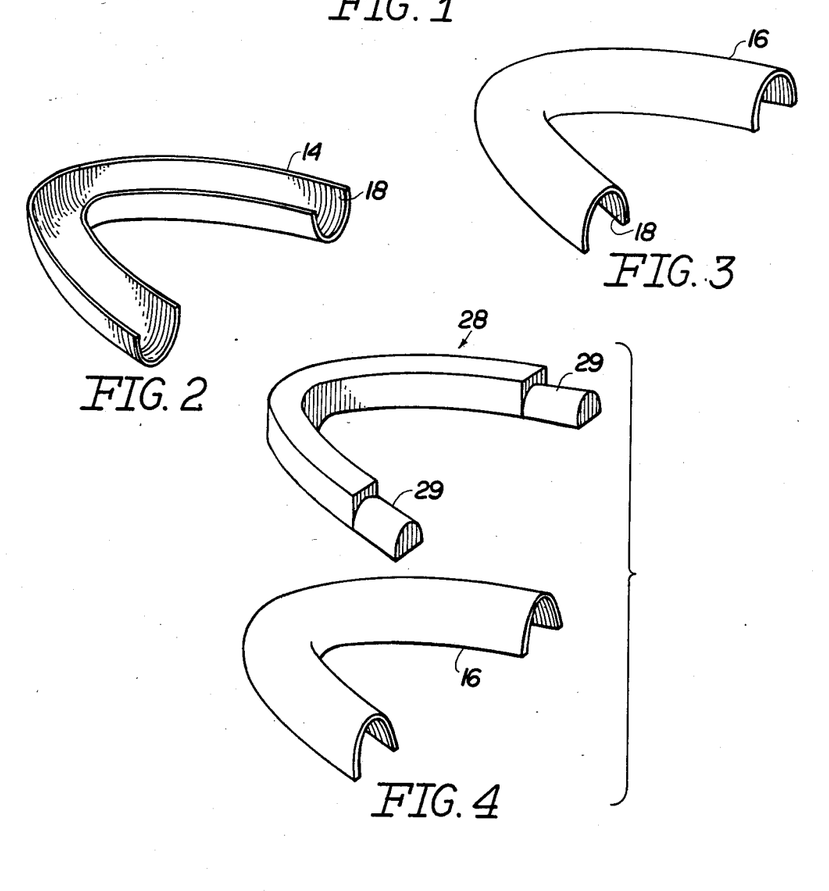
FIG. 2 is an isometric view of an upper denture plate base for complete assembly.
FIG. 3 is a lower denture plate base prior to complete assembly.
FIG. 4 is an isometric view of a wax block and lower plate base used in manufacture but prior to completion.
Figure 5:
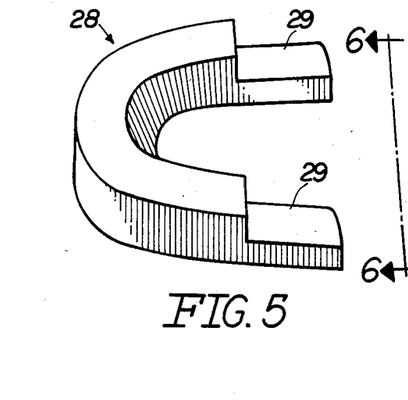
FIG. 5 is an isometric view of the wax block used in formation of the present invention.
Figure 6:
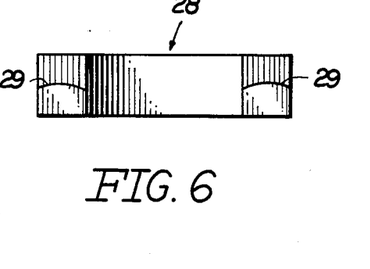
FIG. 6 is an end view along line 6—6 of FIG. 5.
Figures 13, 15:
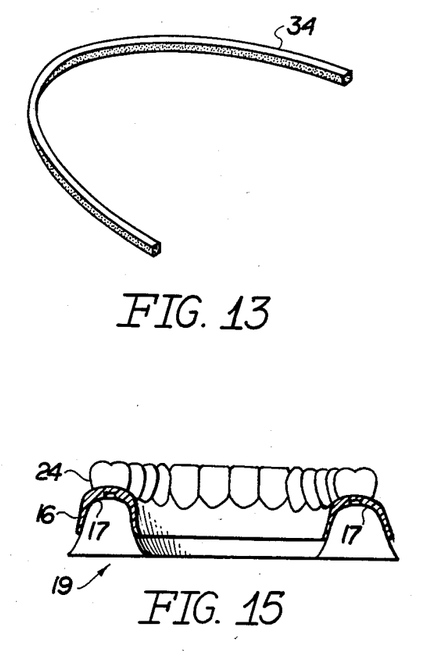
FIG. 13 is an isometric view of a filter element structured for insertion within the differential pressure channel of the present invention.
FIG. 15 is an end view along line 15—15 in FIG. 14.
Figure 14:
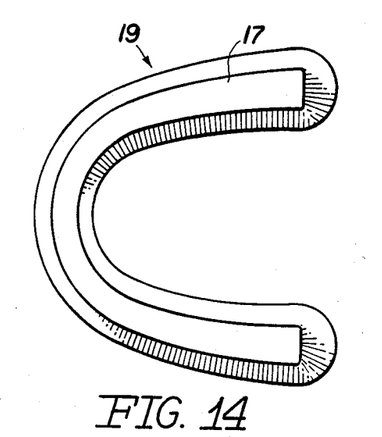
FIG. 14 is a top view of a structure representing an alveolar ridge.
Figure 16:
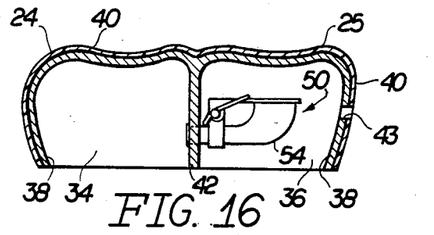
FIG. 16 is a sectional view showing interior portions of designated false teeth components and a one-way flow valve disposed therein.
Figure 17:
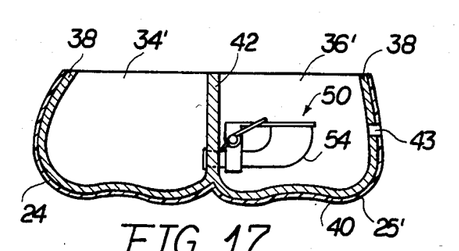
FIG. 17 is a one-way flow valve mounted on the interior of upper teeth components.
Figure 18:
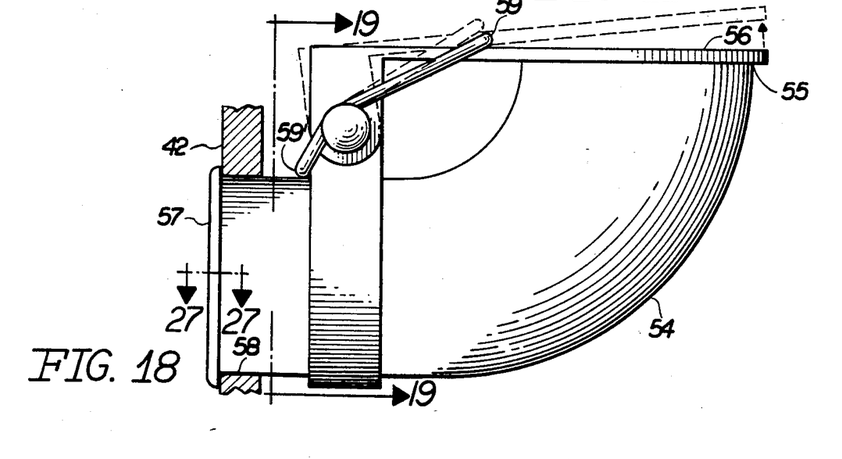
FIG. 18 is a side view of a one-way flow valve with valve head portion represented in broken lines when in its open position.
Figure 19:
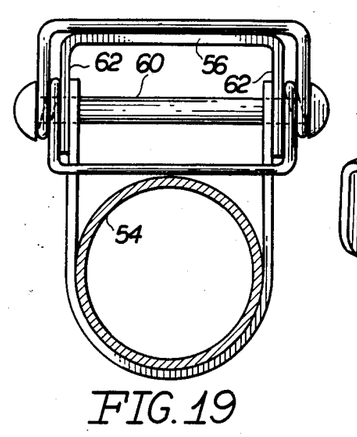
FIG. 19 is sectional view along line 19—19 of FIG. 18 showing interior structural components of the one-way valve structure.
Figure 20:
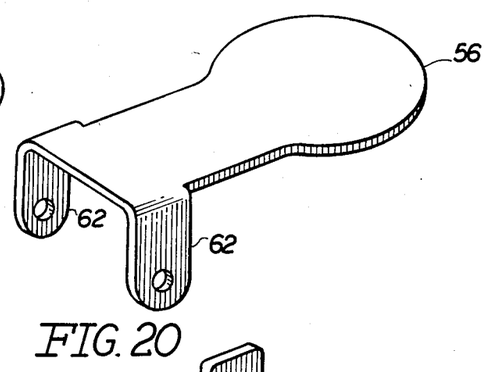
FIG. 20 is an isometric detailed view of a head portion of the valve structure of FIG. 18.
Figure 21:
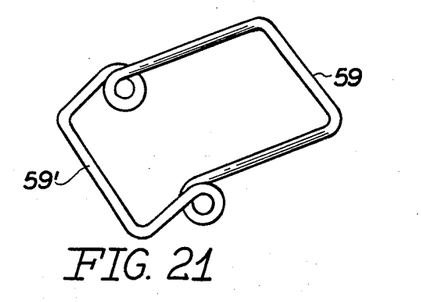
FIG. 21 is a detailed isometric view of the biasing means of the valve structure of FIG. 18.
Figure 22:
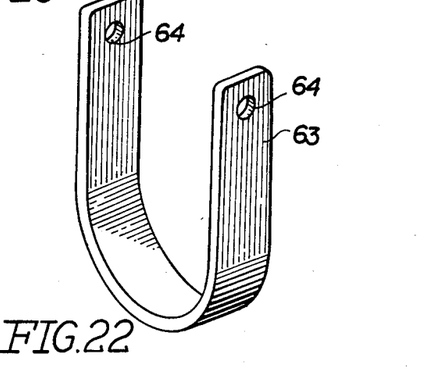
FIG. 22 is an isometric detailed view of a bracket structure of the valve of FIG. 18.

With reference to FIGS. 2 and 3 an upper base 14 and a lower base 16 are provided such that the base portions 14 and 16 of the full plates 12 and 10 respectively have a substantially concave undersurface forming an elongated groove 18 specifically dimensioned and figured to correspond to the overall U-shaped configuration of the alveolar ridge generally indicated as 19 in FIGS. 14 and 15. For purposes of clarity, the alveolar ridge structure 19 is represented in the aforementioned figures only to present the overall general configuration. Such structure is not meant to be an accurate representation of a true alveolar ridge as it exists in the mouth of a wearer.

Further with regard to FIGS. 4 through 8, a brief description is herein supplied of the method of manufacture of the structure of the present invention in the form of denture plates 10 and 12 each having a predetermined ones or full set of individual false teeth 21, 22, 23, etc. However, the specific structural features of the first and second molar 24 and 25 and 24' and 25' on both the lower an upper set respectively is of particular importance and will be discussed in greater detail hereinafter.

In manufacture the base 16 of the lower and upper (not shown) plate are properly fitted to the alveolar ridge of the wearer and a bite block generally indicated as 28, made of wax or like material, is prepared. In such preparation, the endmost portions as at 29 are provided to have an upwardly extended curvature for the acceptance of the anterior teeth or the first and second molar 24 and 25 which are set in place. The extended radius of curvature of the portions 29 of bite block 28 are then reduced in size and dimension. When the "wax-up" portion of the process is completed, the overall configuration will be that as represented in FIG. 7.

Figure 7:
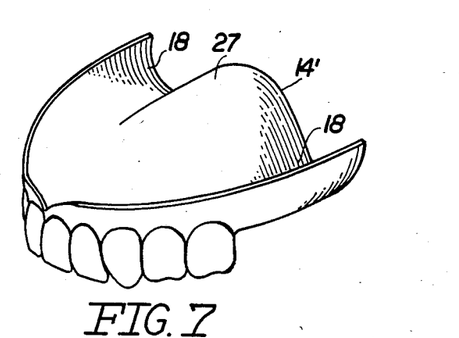
FIG. 7 is a wax model of an upper denture plate with specific false teeth portions and with components of the present invention not yet affixed.
Figure 8:
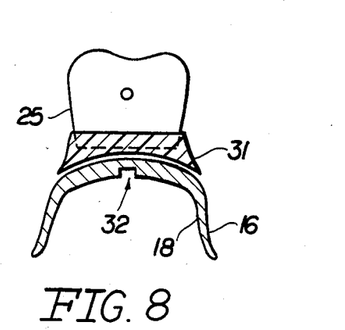
FIG. 8 is a sectional view of a false tooth structure and base of a dental plate including differential pressure channel formed therein.

With specific reference to FIG. 7 a wax-up model is shown with a plurality of false teeth in place absent the anterior first and second molars. However, the model shown in FIG. 7 includes a palate portion 27 in the upper base 14'. However, due to the application of sufficient pressure being applied to the exposed surface of the alveolar ridge, as set forth above, such a palate may in fact not be required since sufficient force exists to prevent or eliminate inadvertent dislodging of the base and specifically the undersurface 18 therefrom during use of the dentures such as in eating. Once the model as in FIG. 7 (with or without palate 27) is completed, the anterior teeth including first and second molars 24 and 25 are properly placed on the upper exposed surface of the base 16 and bonded through the provision of a proper foundation structure 31 of the molars 24 and 25.

Figure 9:
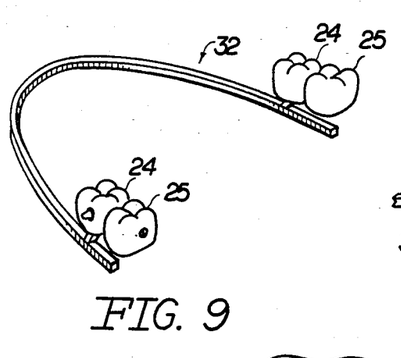
FIG. 9 is an isometric view of the differential pressure channel and certain false teeth components of the present invention without the remainder of the dental plate affixed thereto.
Figure 10:
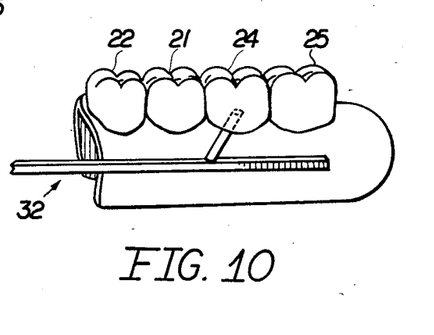
FIG. 10 is an isometric view in partial cutaway showing specific false teeth and structural components of the present invention.

An important structural feature of the present invention is the formation of a differential pressure channel generally indicated as 32 extending along the entire length of the undersurface or channel 18 of each of the plates 14 and 16 and represented schematically in FIGS. 9 and 10 without the supporting structure of the plate 16. Suffice it to say that the differential pressure channel is extended along the entire length of the undersurface of each of the basis 16 and 14 of the dental plates 10 and 12.

Figure 12:
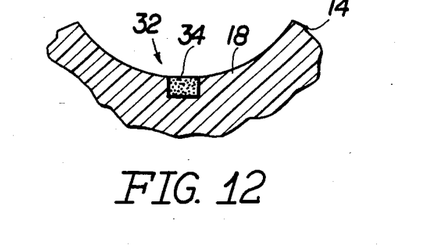
FIG. 12 is a sectional view in partial cutaway showing structural details of a differential pressure channel of the present invention.

Further structural features directly related to the differential pressure channel 32 is the provision of a filter element 34 made of fibrous or like applicable filtering material and effectively packed in and extending along the length of the differential pressure channel 32. As shown in FIG. 12, the filter element 34 may be substantially flush with the undersurface 18 of the base 14 or 16 such that its position prevents particles from entering the channel and further aids in the comfort of positioning the surface 18 on the top or crown portion 17 of the alveolar ridge 19 FIGS. 14 and 15).

In operation, either a complete dental plate 10 or 12 (FIG. 1) or a partial dental plate 12' (FIG. 28) is maintained in proper operative position on the exposed surface of the alveolar ridge (see FIG. 15) through the creation and maintenance of a partial vacuum between the undersurface 18 of the base 16 especially along the area and length of the alveolar ridge 32 and the exposed surface of the alveolar ridge itself 19. The creation and maintenance of such partial vacuum is accomplished through the creation by the wearer in the mouth of a partial vacuum, easily attainable, and the existence of certain valving structure within predetermined false teeth wherein the individual structures of the false teeth and the valving structure will be herein described in detail with specific reference to FIGS. 16 through 29.

Figure 11:
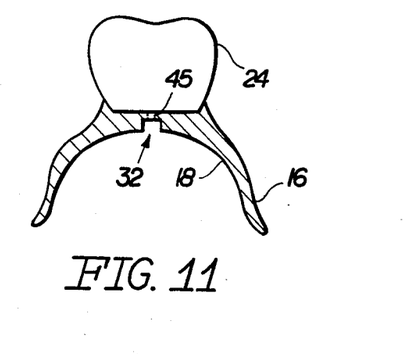
FIG. 11 is a sectional view through the base of a dental plate with a false tooth affixed thereto.
Figure 29:
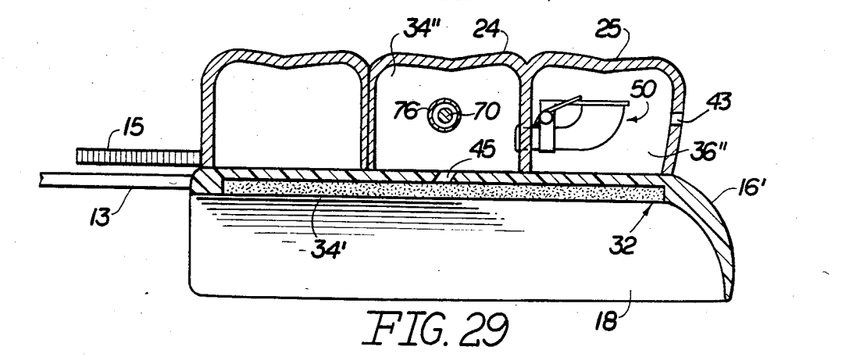
FIG. 29 is a sectional view in partial cutaway along line 29—29 of FIG. 28.

Predetermined ones of the false teeth, preferably first and second molars 24 and 25 and/or 24' and 25' have a hollow interior portion comprising a first chamber 34 and a second chamber 36. The specific structure of first and second molars 24, 25 is essentially a unitary construction wherein a metal outer casing 38, or like rigid material, is configured to the predetermined design and configuration of molars or other predetermined teeth configuration. A facing coating such as a porcelain or any material resembling enamel in appearance as enamel 40 is placed over the molars for purposes of aesthetics. The first and second chambers 34 and 36 respectively are somewhat segregated by a common internal wall 42 which preferably is integrally formed with the casing 38. Passage means are provided in the form of an aperture 43 disposed in fluid communication between the hollow interior or specifically second chamber 36 and the exterior of the molar pair 24, 25. As best shown in FIGS. 10, 11 and 29, the passage means further comprises a passage or aperture 45 disposed in a top portion of the base 16' wherein such passage or aperture 45 is established in direct fluid communication between the differential pressure channel 32 and the hollow interior portion of the molar pair 24, 25 and specifically the first chamber 34.

Figure 23:
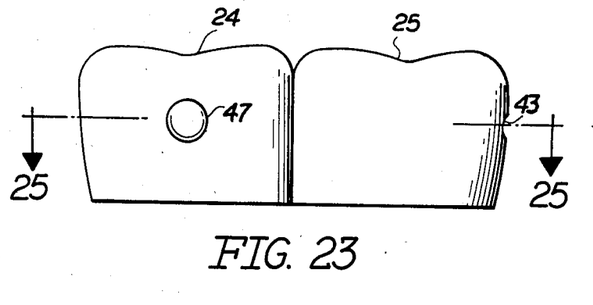
FIG. 23 is a side view of a first and a second false tooth defining the hollow interior portion of the false teeth of the present invention.
Figure 26:
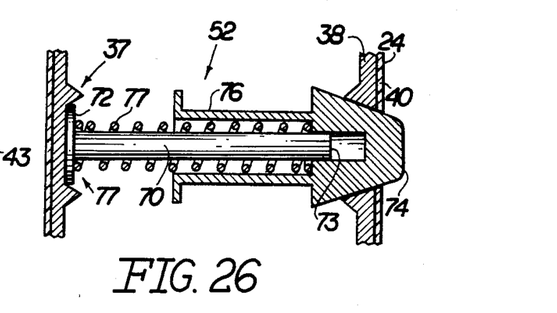
FIG. 26 is a sectional view along line 26—26 of FIG. 25 showing structural details of the venting valve structure of the present invention.
Figure 27:
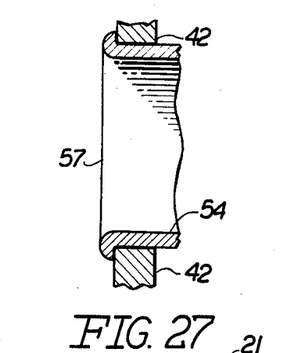
FIG. 27 is a sectional view in partial cutaway of the exit aperture of the venting valve structure.

With reference to FIGS. 23 and 26, the passage means further comprises an aperture 47 formed in an exposed side wall of the first molar 24 and disposed to establish direct fluid communication with the exterior of the molar pair 24, 25 and the first chamber 24 or the hollow interior portion of which first chamber 24 is a part. Further, aperture 47 defines a valve seat for a valve head associated with venting valve structure generally indicated at 52. Function of the individual passages 43, 45 and 47 will become clear upon a detailed discussion of the structure of the valving means comprising a one-way flow valve generally indicated as 50 and a venting valve generally indicated as 52.

With primary reference to FIGS. 16 through 22, the valve means of the present invention comprises the one-way flow valve 50 being mounted within second chamber 36 of the second molar 25 of each molar pair. One-way flow valve 50 comprises a conduit 54 having an entrance or opening as at 55 covered by a head or lid element 56. The conduit 54 has an exit or second opening 57 at the opposite end thereof wherein the peripheral lip of the opening 57 is enlarged for secure mounting of a reduced diameter portion 58 of conduit 54 within an appropriately formed aperture in the common wall 42. By virtue of this disposition the entrance aperture 55 is maintained, as is most of the structure of the one-way flow valve 50, in the second chamber 36 but is structured to establish direct fluid communication with the first chamber 34 by virtue of the disposition of the opposite end opening 57 of conduit 54. A biasing means comprises a spring element 59 secured in its open, biasing position about pivot pin 60 such that depending ears 62 of the head or lid 56 are disposed and structured to allow pivotal movement of the entire lid 56 about the longitudinal axis of the pivot pin 60 when the lid moves and acts against the biasing force exerted thereon by the spring element 59. The opposite end as at 59' of the spring element is secured against a support bracket 63 which also serves to support the pivot pin 60 by the provision of aligned apertures 64. By virtue of the structure of the biasing means, the lid 56 is normally biased in its closed position. However, upon a creation of a negative pressure within the mouth of the wearer sufficient force will be exerted thereon to effectively lift the lid 56 (see broken lines FIG. 18) and allow fluid flow from the differential pressure channel 32 through passage or aperture 45 of the first chamber 34 and further through the conduit 54 of the one-way flow valve out the entrance 55 and through second chamber 36 to the exterior of the molar pair 24, 25 through aperture 43.

Figure 24:
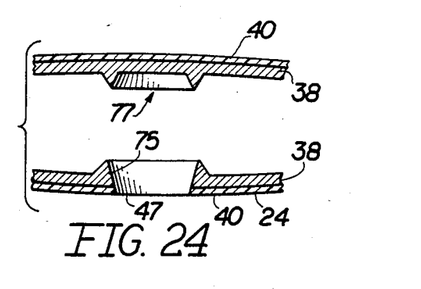
FIG. 24 is a sectional view in partial cutaway showing the structural details of a valve seat and receiving portion for structural components of a venting valve structure as shown in FIG. 26.

Once a partial vacuum has been established within the differential pressure channel 32, the valving means of the present invention further comprises a venting valve 52 disposed and structured to relieve the negative pressure and release the partial vacuum either totally or in part. Such release is necessary of course to remove the plates from the aveolar ridge 19 such as for cleaning and maintenance. In addition, the wearer of the plates may want to establish a greater pressure during actual use as in chewing which would not be comfortable for an entire day's wear of the dental plate. In such situations, the venting valve 52 may be activated to reduce the negative pressure of the partial vacuum but not to eliminate it entirely. Therefore, the venting valve comprises a valve stem 70 having a base portion 72 and the opposite end as at 73 attached to valve head 74. The valve head 74 has an outer surface configuration substantially corresponding to the tapered periphery of aperture 47 as at 75 (FIG. 24). A sheath or sleeve 76 is used to house a biasing spring 77 which is positioned to normally force or bias the valve head 74 into its closed, seated relation within the aperture 47 defining the valve seat as set forth above, Further, the base 72 of the stem 70 is seated within an indentation 77 integrally formed in the internal surface of the casing 38 as best shown in 34.

Figure 25:
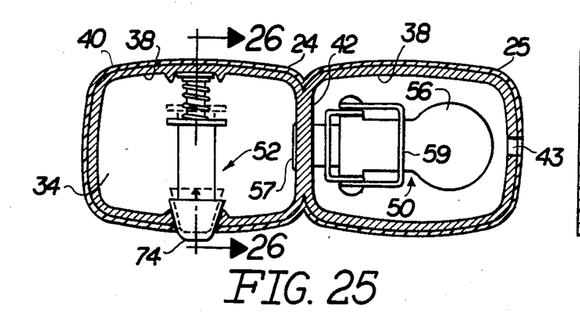
FIG. 25 is a sectional view showing interior structural components of the valving structures and taken along line 25—25 of FIG. 23.

In operation, a fingernail or like applicable tool can be used to depress the head 74 out of its closed or sealing position relative to the aperture seat 47 as best shown in broken lines in FIG. 25. Such open positioning will allow communication between the differential pressure channel 32, passage 45, interior of first channel 34 and the aperture 47 thereby allowing communication of the differential pressure channel 32 with surrounding atmosphere.

Figure 28:
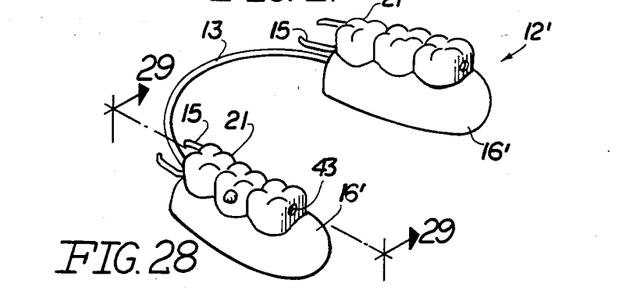
FIG. 28 is an isometric view of another embodiment comprising a partial dental plate.

Another structural feature of the present invention is best represented in FIGS. 28 and 29 wherein the dental plate 12' is in fact a partial plate having base plate segments 16' interconnected by a brace element such as a wire 13. Further gripping snap-like connectors 15 extend outwardly from foremost false teeth 21 which is essentially separate from but disposed adjacent to the individual first and second molars 24 and 25.

With reference to FIG. 29 each base segment includes an undersurface 18 dimensioned and configured to fit over predetermined parts of the aveolar ridge 19 wherein the differential pressure channel 34' represents a channel segment portion which extends only the length of the individual base segments 16' as shown in FIG. 29.

Figure 30:
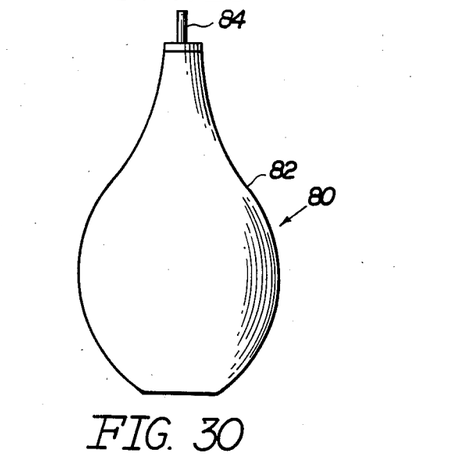
FIG. 30 is a front plan view of a syringe structure associated with cleaning of components of the present invention.

Finally, additional tools which may be utilized to maintain cleanliness of the overall structure includes a syringe-type structure generally indicated as 80 having a collapsible wall 82 and a nozzle 84 wherein cleaning fluid may be directed through the differential pressure channel 34 or channel segments 34' in order to force cleaning fluid therethrough and to various passages into the interior portions of the molar pairs 24, 25.

What is claimed is:

1. A dental prosthesis structure primarily designed to be secured within the mouth of the user through the application of a partial vacuum, said structure comprising:
    (a) dental plate means structured for mounting along a predetermined length of an alveolar ridge of the user and including at least one dental plate having an undersurface configured and dimensioned for sealing engagement with an exposed surface portion of the alveolar ridge,
    (b) channel means comprising a differential pressure channel formed in said plate undersurface and disposed to extend along at least a portion of the length of said dental plate and in fluid communicating relation with the exposed surface portion of the alveolar ridge,
    (c) teeth means secured to said dental plate and protruding from an outer surface thereof, said teeth means including a hollow interior portion comprising a first chamber disposed in direct fluid communication with said differential pressure channel and a second chamber structured for direct communication with atmosphere and the exterior of said hollow interior portion,
    (d) valve means mounted on said teeth means and disposed in fluid regulating relation between said differential pressure channel and the exterior of said teeth means,
    (e) said valve means comprising a one-way flow valve structured to permit fluid flow from said channel means to said teeth means to the exterior thereof and prohibit fluid flow therethrough to said differential pressure channel from the exterior of said teeth means,
    (f) said valve means further comprising a venting valve mounted within said hollow interior portion and in communicating relation with the exterior of said teeth means, said venting valve disposed and structured to regulate fluid flow from the exterior of said teeth means to said differential pressure channel,
    whereby creation of a negative pressure within the mouth establishes a negative pressure within said differential pressure channel and sealed engagement between said plate undersurface and the alveolar ridge.

2. A structure as in claim 1 wherein said venting valve comprises a valve seat disposed and structured to at least partially define an aperture within a wall portion of said teeth means, said aperture disposed in fluid communicating relation between said hollow interior portion and the exterior of said teeth means; said venting valve further including a valve head and a biasing means disposed to normally bias said valve head into sealing engagement with said valve seat and said aperture.

3. A structure as in claim 2 wherein said valve head is accessible through said aperture from the exterior of said teeth means and selectively disposable out of its closed, seated position and against biasing force of said biasing means, whereby fluid flow through said venting valve substantially eliminates said negative pressure between said differential pressure channel and the alveolar ridge.

4. A structure as in claim 1 further comprising passage means including a first passage disposed in interconnecting relation between said differential pressure channel and said first chamber; said passage means including a second passage disposed in interconnecting relation between said second chamber and the exterior of said teeth means, whereby fluid flow is established from said differential pressure channel to the exterior of said teeth means via said passage means and valve means.

5. A structure as in claim 1 wherein said venting means includes biasing means disposed and structured to normally position said venting valve in a closed position, said venting valve accessible to the exterior of said teeth means and disposed and structured for selective manipulation and attendant positioning into an open, fluid venting position.

6. A structure as in claim 5 wherein said venting valve is mounted within said first chamber in fluid regulating relation between said differential pressure channel and the exterior of said hollow interior portion, said one-way flow valve being mounted within said second chamber in fluid regulating relation between said differential pressure channel and the exterior of said teeth means via said first and said second chamber respectively.

7. A structure as in claim 1 wherein said one-way flow valve is mounted within said second chamber and comprises a conduit means disposed in interconnecting relation between said first and said second chambers and including an entrance disposed within said second chamber and an exit disposed within said first chamber, a head portion normally biased in closed, sealing relation to said entrance, said head portion disposed and strutured for selective movement to an open position relative to said entrance upon the application of negative pressure to said hollow interior portion, whereby fluid flow is established through said one-way flow valve from said differential pressure channel to the exterior of said teeth means.

8. A dental prosthesis structure primarily designed to be secured within the mouth of the user through the application of a partial vacuum, said structure comprising:
(a) dental plate means structured for mounting along a predetermined length of an alveolar ridge of the user and including at least one dental plate having an undersurface configured and dimensioned for sealing engagement with an exposed surface portion of the alveolar ridge,
(b) channel means comprising a differential pressure channel formed in said plate undersurface and disposed to extend along at least a portion of the length of said dental plate and in fluid communicating relation with the exposed surface portion of the alveolar ridge,
(c) teeth means secured to said dental plate and protruding from an outer surface thereof, said teeth means including a hollow interior portion comprising a first chamber disposed in direct fluid communication with said differential pressure channel and a second chamber structured for direct communication with atmosphere and the exterior of said hollow interior portion,
(d) said teeth means comprising a first tooth and a second tooth structured to substantially define an outer casing for said first and said second chamber respectively, said first tooth and said second tooth each fixedly mounted on said one dental plate in adjacent relation to one another,
(e) valve means mounted on said teeth means and disposed in fluid regulating relation between said differential pressure channel and the exterior of said teeth means, said valve means disposed and structured to regulate and establish fluid flow between said first chamber and said second chamber,
(f) said valve means comprising a one-way flow valve structured to permit fluid flow from said channel means to said teeth means to the exterior thereof and prohibit fluid flow therethrough to said differential pressure channel from the exterior of said teeth means, and
(g) whereby creation of a negative pressure within the mouth establishes a negative pressure within said differential pressure channel and sealed engagement between said plate undersurface and said alveolar ridge.

9. A structure as in claim 8 wherein said one dental plate comprises a full plate structure configured to correspond to and extend along substantially the entire length of an alveolar ridge, said differential pressure channel extending substantially along the entire length of said plate undersurface in fluid communicating relation with the exposed surface portion of the alveolar ridge.

10. A structure as in claim 9 wherein said teeth means comprises a first and a second hollow interior portion each disposed in spaced relation to one another along the length of said full plate structure and in fluid communication with said differential pressure channel; said valve means comprising a one-way flow valve mounted within each of said hollow interior portions and structured to permit one-way fluid flow from spaced apart portions of said differential pressure channel to the exterior of said respective hollow interior portions.

11. A structure as in claim 10 wherein each of said hollow interior portions are disposed at a substantially opposite end of said full plate structure and comprise a first chamber disposed in direct fluid communication with said differential pressure channel and a second chamber structured for direct communication with atmosphere and the exterior of said respective hollow interior portions, said valve means disposed and structured to regulate and establish fluid flow between said first chamber and said second chamber of respective hollow interior portions.

12. A structure as in claim 11 wherein said valve means further comprises a venting valve mounted within said first chamber of each hollow interior portion in fluid regulating relation between said differential pressure channel and the exterior of said respective hollow interior portions, said one-way flow valve being mounted within said second chamber of each hollow interior portion in fluid regulating relation between said differential pressure channel and the exterior of said teeth means via said first and said second chamber respectively.

13. A structure as in claim 8 wherein said one dental plate further comprises a partial plate structure including two plate segments disposed in connected and spaced apart relation to one another and each plate segment configured and structured to include an undersurface disposed in sealing and mating, supported engagement with spaced apart exposed surface portions of the alveolar ridge, said teeth means secured to each plate segment and including respective hollow interior portions.

14. A structure as in claim 13 wherein said differential pressure channel comprises a channel segment integrally formed in said undersurface of each plate segment and in fluid communication with respect to the hollow interior portions of each segment; said valve means comprising a one-way flow valve mounted within each of said hollow interior portions and structured to permit one-way fluid flow from spaced apart portions of said differential pressure channel to the interior of said respective hollow interior portions.

15. A structure as in claim 14 wherein each of said hollow interior portions are disposed at substantially opposite ends of said partial plate structure and comprise a first chamber disposed in direct fluid communication with said differential pressure channel and a second chamber structured for direct communication with atmosphere and the exterior of said respective hollow interior portion, said valve means disposed and structured to regulate and establish fluid flow between said first chamber and said second chamber.

16. A structure as in claim 15 wherein said valve means further comprises a venting valve mounted within said first chamber of each hollow interior portion in fluid regulating relation between said differential pressure channel and the exterior of said respective hollow interior portion, said one-way flow valve being mounted within said second chamber of each hollow interior portion in fluid regulating relation between said differential pressure channel and the exterior of said teeth means via said first and said second chamber respectively.

17. A structure as in claim 8 wherein said first tooth and said second tooth are integrally connected to one another and comprise a common wall disposed in substantially segregated relation between said first and said second chamber; said valve means further comprising a venting valve disposed within said first tooth and in fluid regulating relation between said differential pressure channel and the exterior of said first tooth, said one-way flow valve disposed within said second tooth in fluid regulating relation between said second chamber and the exterior of said first tooth.

18. A structure as in claim 17 further comprising passage means including a first passage disposed in interconnecting relation between said differential pressure channel and said first chamber; said passage means including a second passage formed in an exposed wall of said second tooth and in interconnecting relation between said second chamber and the exterior of said second tooth, a third passage at least partially defining a valve seat of said venting valve and formed in an exposed wall of said first tooth, whereby fluid flow is selectively established from said differential pressure channel to the exterior of said teeth means via said passage means and said valve means.

19. A structure as in claim 8 wherein said first tooth and said second tooth are formed from a substantially rigid material and include a facing material secured to and substantially encasing the outer surface thereof, each tooth being structured and configured to resemble a predetermined human tooth.

20. A dental prosthesis structure primarily designed to be secured within the mouth of the user through the application of a partial vacuum, said structure comprising:

(a) dental plate means structured for mounting along a predetermined length of an alveolar ridge of the user and including at least one dental plate having an undersurface configured and dimensioned for sealing engagement with an exposed surface portion of the alveolar ridge, (b) channel means comprising a differential pressure channel formed in said plate undersurface and disposed to extend along at least a portion of the length of said dental plate and in fluid communicating relation with the exposed surface portion of the alveolar ridge, (c) teeth means secured to said dental plate and protruding from an outer surface thereof, said teeth means including a hollow interior portion disposed, at least in part, in communicating relation with said channel means and ambient atmosphere exterior of said teeth means, (d) valve means mounted on said teeth means and disposed in fluid regulating relation between said differential pressure channel and the exterior of said teeth means, (e) said valve means comprising a one-way flow valve structured to permit fluid flow from said channel means to said teeth means to the exterior thereof and prohibit fluid flow therethrough to said differential pressure channel from the exterior of said teeth means, (f) filter means having a substantially elongated configuration and dimensioned and structured to fit at least partially within said differential pressure chamber along at least a portion of its length, said filter means provided for the collection of debris particles and the prevention thereof from entering said hollow interior portion through said differential pressure channel.

* * * * *